United States Patent
Xu et al.

(10) Patent No.: US 9,901,523 B2
(45) Date of Patent: *Feb. 27, 2018

(54) ORAL CARE PRODUCTS COMPRISING ZINC OXIDE AND TRIMETHYLGLYCINE

(71) Applicant: Colgate-Palmolive Company, Piscataway, NJ (US)

(72) Inventors: Guofeng Xu, Plainsboro, NJ (US); Zhiqiang Liu, Bridgewater, NJ (US); Long Pan, Cherry Hill, NJ (US); LaTonya Kilpatrick-Liverman, Princeton, NJ (US); Ying Yang, Monmouth Junction, NJ (US); Michael A. Stranick, Bridgewater, NJ (US); Zhigang Hao, Bridgewater, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/653,885

(22) PCT Filed: Dec. 19, 2012

(86) PCT No.: PCT/US2012/070537
§ 371 (c)(1),
(2) Date: Jun. 19, 2015

(87) PCT Pub. No.: WO2014/098829
PCT Pub. Date: Jun. 26, 2014

(65) Prior Publication Data
US 2015/0328112 A1 Nov. 19, 2015

(51) Int. Cl.
*A61K 8/27* (2006.01)
*A61K 8/44* (2006.01)
*A61K 8/20* (2006.01)
*A61K 8/21* (2006.01)
*A61Q 11/00* (2006.01)

(52) U.S. Cl.
CPC ............... *A61K 8/27* (2013.01); *A61K 8/20* (2013.01); *A61K 8/21* (2013.01); *A61K 8/44* (2013.01); *A61Q 11/00* (2013.01); *A61K 2800/58* (2013.01); *A61K 2800/92* (2013.01)

(58) Field of Classification Search
None
See application file for complete search history.

(56) References Cited

U.S. PATENT DOCUMENTS

| | | |
|---|---|---|
| 2,503,280 A | 4/1950 | Lockwood |
| 2,507,088 A | 5/1950 | Bradley |
| 2,527,686 A | 10/1950 | Sandberg |
| 2,893,918 A | 7/1959 | Abramson |
| 3,260,744 A | 7/1966 | Kenkichi |
| 3,320,174 A | 5/1967 | Rubinfeld |
| 3,372,188 A | 3/1968 | Terence |
| 3,535,421 A | 10/1970 | Briner |
| 3,538,730 A | 11/1970 | Morton |
| 3,678,154 A | 7/1972 | Briner |
| 3,741,911 A | 6/1973 | Shane |
| 3,862,307 A | 1/1975 | Giulio |
| 3,937,807 A | 2/1976 | Haefele |
| 3,941,818 A | 3/1976 | Abdel-Monem |
| 3,959,458 A | 5/1976 | Agricola et al. |
| 4,051,234 A | 9/1977 | Gieske et al. |
| 4,316,824 A | 2/1982 | Pancheri |
| 4,339,432 A | 7/1982 | Ritchey et al. |
| 4,340,583 A | 7/1982 | Wason |
| 4,487,757 A | 12/1984 | Kiozpeoplou |
| 4,565,693 A | 1/1986 | Marschner |
| 4,599,152 A | 7/1986 | Ashmead |
| 4,684,528 A | 8/1987 | Godfrey |
| 4,687,663 A | 8/1987 | Schaeffer |
| 4,842,847 A | 6/1989 | Amjad |
| 4,866,161 A | 9/1989 | Sikes et al. |
| 4,885,155 A | 12/1989 | Parran, Jr. et al. |
| 5,004,597 A | 4/1991 | Majeti et al. |
| 5,061,815 A | 10/1991 | Leu |
| 5,156,845 A | 10/1992 | Grodberg |
| 5,188,821 A | 2/1993 | Gaffar et al. |
| 5,192,531 A | 3/1993 | Gaffar et al. |
| 5,310,545 A * | 5/1994 | Eisen .............. A61K 8/4946 424/49 |
| 5,330,748 A * | 7/1994 | Winston ............. A61K 8/27 424/49 |
| 5,504,055 A | 4/1996 | Hsu |

(Continued)

FOREIGN PATENT DOCUMENTS

| | | |
|---|---|---|
| CA | 1105389 A1 * | 7/1981 |
| CN | 1502329 | 6/2004 |

(Continued)

OTHER PUBLICATIONS

Anonymous, "Zinc Lauryl Ether Sulphate, A New Approach to Skincare,", Apr. 2004, Retrieved from Internet, http://www.erwebhosting.it/zsi/repository/Zinc%20Lauryl%20Ether %20Sulphate,%20A%20new%20approach%20to%20skin%20care.pdf, Retrieved Sep. 26, 2013.

Deschaume et al., "Interactions of aluminum hydrolytic species with biomolecules," New Journal of Chemistry, 2008, 32:1346-1353.

European Food Safety Authority, "Scientific Opinion on the safety and efficacy of tetra-basic zinc chloride for all animal species," EFSA Journal, 2012, 10(5):2672.

Hartwell et al., "Preparation and characterization of tyrosine and lysine metal chelate polyesters and polyamides", J. of the American Chem. Society, Mar. 1970, 92(5):1284-1289.

(Continued)

*Primary Examiner* — Frederick Krass
*Assistant Examiner* — Michael P Cohen

(57) ABSTRACT

Described herein are oral care compositions comprising a mixture of zinc oxide and trimethylglycine, in free or orally acceptable salt form. Methods of making and using the compositions are also provided.

16 Claims, No Drawings

(56) References Cited

U.S. PATENT DOCUMENTS

| | | | |
|---|---|---|---|
| 5,643,559 A | 7/1997 | Eigen et al. | |
| 5,658,554 A * | 8/1997 | Fisher | A61K 33/42 424/49 |
| 5,698,724 A | 12/1997 | Anderson et al. | |
| 5,707,679 A | 1/1998 | Nelson | |
| 5,714,447 A | 2/1998 | Jones et al. | |
| 5,911,978 A | 6/1999 | Carr et al. | |
| 5,993,784 A | 11/1999 | Hill | |
| 6,121,315 A | 9/2000 | Nair et al. | |
| 6,156,293 A * | 12/2000 | Jutila | A61K 8/416 424/422 |
| 6,607,711 B2 | 8/2003 | Pedersen | |
| 6,610,274 B1 * | 8/2003 | Gardner | A61K 31/65 424/49 |
| 6,685,920 B2 | 2/2004 | Baig et al. | |
| 6,969,510 B2 | 11/2005 | Holerca et al. | |
| 8,067,627 B2 | 11/2011 | Newsome et al. | |
| 8,247,398 B2 | 8/2012 | Goel | |
| 2004/0042978 A1 | 3/2004 | Embro | |
| 2004/0122088 A1 | 6/2004 | Newsome et al. | |
| 2004/0033916 A1 | 10/2004 | Holerca et al. | |
| 2004/0198998 A1 | 10/2004 | Holerca et al. | |
| 2006/0024252 A1 | 2/2006 | Esposito et al. | |
| 2007/0071698 A1 | 3/2007 | Doss | |
| 2009/0176719 A1 * | 7/2009 | Goldstein | A61K 31/397 514/29 |
| 2009/0220444 A1 | 9/2009 | Teckenbrock et al. | |
| 2010/0021573 A1 | 1/2010 | Gonzalez et al. | |
| 2010/0266480 A1 | 10/2010 | Huang | |
| 2010/0330163 A1 | 12/2010 | Soparkar | |
| 2011/0076309 A1 | 3/2011 | Misner et al. | |
| 2011/0229536 A1 | 9/2011 | Kvitnitsky et al. | |
| 2013/0017240 A1 | 1/2013 | Porter et al. | |
| 2014/0170086 A1 | 6/2014 | Pan et al. | |

FOREIGN PATENT DOCUMENTS

| | | |
|---|---|---|
| CN | 1519227 | 8/2004 |
| CN | 101606639 | 12/2009 |
| CN | 102014858 | 4/2011 |
| CN | 102811698 | 12/2012 |
| CN | 103156073 | 6/2013 |
| CN | 103535536 | 1/2014 |
| DE | 735096 | 5/1943 |
| EP | 0083486 | 12/1982 |
| EP | 0108937 | 5/1984 |
| EP | 0508524 | 10/1992 |
| EP | 0514553 | 11/1992 |
| EP | 0842664 | 5/1998 |
| EP | 1021158 | 7/2000 |
| EP | 1064946 | 1/2001 |
| EP | 1203575 | 5/2002 |
| EP | 1319394 | 6/2003 |
| EP | 1935395 | 6/2008 |
| EP | 1529775 | 5/2011 |
| FR | 2241301 | 3/1975 |
| GB | 2052978 | 2/1981 |
| GB | 2109685 | 6/1983 |
| GB | 2243775 | 11/1991 |
| JP | S57-156329 A | 9/1982 |
| JP | S57-158724 | 9/1982 |
| JP | 2004175790 | 6/2004 |
| JP | 2006-131522 A | 5/2005 |
| JP | 2009084201 | 4/2009 |
| JP | 2010132639 | 6/2010 |
| RU | 2432150 | 10/2011 |
| WO | WO86/00004 | 1/1986 |
| WO | WO9917735 | 4/1999 |
| WO | WO199917735 | 4/1999 |
| WO | WO0169087 | 9/2001 |
| WO | WO2004054531 | 7/2004 |
| WO | WO2004/064536 | 8/2004 |
| WO | WO2007063507 | 6/2007 |
| WO | WO2011053291 | 5/2011 |
| WO | WO2011/088199 | 7/2011 |
| WO | WO2011/123123 | 10/2011 |
| WO | WO2014/098813 | 6/2014 |
| WO | WO2014/098814 | 6/2014 |
| WO | WO2014/098818 | 6/2014 |
| WO | WO2014/098819 | 6/2014 |
| WO | WO2014/098821 | 6/2014 |
| WO | WO2014/098822 | 6/2014 |
| WO | WO2014/098824 | 6/2014 |
| WO | WO2014/099164 | 6/2014 |
| WO | WO2014/099165 | 6/2014 |
| WO | WO2014/099166 | 6/2014 |
| WO | WO2014/099167 | 6/2014 |
| WO | WO2014098825 | 6/2014 |
| WO | WO2014098826 | 6/2014 |
| WO | WO2014098828 | 6/2014 |
| WO | WO2014098829 | 6/2014 |
| WO | WO2014099039 | 6/2014 |
| WO | WO2014099226 | 6/2014 |
| WO | WO2014204439 | 12/2014 |

OTHER PUBLICATIONS

International Search Report and Written Opinion for International Application No. PCT/US2012/070489 dated Oct. 22, 2013.
International Search Report and Written Opinion for International Application No. PCT/US2012/070492 dated Oct. 22, 2013.
International Search Report and Written Opinion for International Application No. PCT/US2012/070498 dated Sep. 4, 2013.
International Search Report and Written Opinion for International Application No. PCT/US2012/070501 dated Oct. 21, 2013.
International Search Report and Written Opinion for International Application No. PCT/US2012/070505 dated Nov. 20, 2013.
International Search Report and Written Opinion for International Application No. PCT/US2012/070506 dated Oct. 14, 2013.
International Search Report and Written Opinion for International Application No. PCT/US2012/070513 dated Oct. 14, 2013.
International Search Report and Written Opinion for International Application No. PCT/US2012/070521 dated Sep. 30, 2013.
International Search Report and Written Opinion for International Application No. PCT/US2012/070525 dated Sep. 27, 2013.
International Search Report and Written Opinion for International Application No. PCT/US2012/070528 dated Sep. 30, 2013.
International Search Report and Written Opinion for International Application No. PCT/US2012/070534 dated Sep. 26, 2013.
International Search Report and Written Opinion for International Application No. PCT/US2012/070537 dated Oct. 11, 2013.
International Search Report and Written Opinion for International Application No. PCT/US2013/046268 dated Apr. 22, 2014.
International Search Report and Written Opinion for International Application No. PCT/US2013/050845 dated Aug. 13, 2014.
International Search Report and Written Opinion for International Application No. PCT/US2013/068852 dated Nov. 10, 2014.
International Search Report and Written Opinion for International Application No. PCT/US2013/068854 dated Oct. 20, 2014.
International Search Report and Written Opinion for International Application No. PCT/US2013/068859 dated Aug. 4, 2014.
International Search Report and Written Opinion for International Application No. PCT/US2013/068860 dated Oct. 22, 2014.
International Search Report and Written Opinion for International Application No. PCT/US2013/070932 dated Jul. 24, 2014.
International Search Report and Written Opinion for International Application No. PCT/US2014/042947 dated Aug. 22, 2014.
International Search Report and Written Opinion for International Application No. PCT/US2014/042948 dated Aug. 26, 2014.
International Search Report and Written Opinion for International Application No. PCT/US2014/043051 dated Feb. 18, 2015.
Kondrot, "The Importance of Zinc," http://www.healingtheeye.com/Articles/zinc.html, Feb. 21, 2012.
Liang et al., "In vitro scratch assay: a convenient and inexpensive method for analysis of cell migration in vitro," Nature Protocols, 2007, 2(2):329-333.

(56) References Cited

OTHER PUBLICATIONS

Liu et al., "The research on zinc coordination number 5 odd structure in zinc complex with L-lysine," J. Molecular Science, 2000, 16(2):114-117, abstract only in English.
Lu et al., "Albumin as a zinc carrier: properties of its high affinity zinc-binding site", Biochem. Soc. Trans., 2008, 36:1317-1321.
Lynch, "Zinc in the mouth, its interactions with dental enamel and possible effects on caries: a review of the literature," Int. Dent. J., Aug. 2011, Suppl 3:46-54.
Mavromichalis et al., "Growth-promoting efficacy of pharmacological doses of tetrabaic zinc chloride in diets for nursery pigs," Canadian Journal of Animal Science, pp. 387-391, Jan. 2001.
McAuliffe et al., "Metal complexes of sulphur-containing amino acids," Inorganica Chimica Acta Reviews, Dec. 1972, 6:103-121.
Moore et al., "Antibacterial activity of gutta-percha cones attributed to the zinc oxide component," Oral Surgery, 1982, 53:508-517.
Mosmann, "Rapid colorimetric assay for cellular growth and survival: Application to proliferation and cytotoxicity assays," J. Immunol. Methods, 1983, 65:55-63.
Pashley et al. Dentin permeability effects of desensitizing dentifrices in vitro. J Periodontol. 1984;55(9):522-525.
Prasad, "Zinc:role in immunity, oxidative stress and chronic inflammation," Current Opinion in Clinical Nutrition and Metabolic Care, 2009, 12:646-652.
Rigano, I., Zinc Lauryl Ether Sulphate—A New Approach to Skin Care, SOFW Journal, Apr. 2004, 128:26-33.
Schmetzer et al., "Wulfingite, ε-Zn(OH)2, and simonkolleite, Zn5(OH)8Cl2•H2O, two new minerals from Richelsdorf, Hesse, F.R.G.," N. Jb. Miner. Mh., Apr. 1985, pp. 145-154.
Seil et al., "Antibacterial effect of zinc oxide nanoparticles combined with ultrasound," Nanotechnology,2012, 23:495101.
Soderling et al., "Betaine-containing toothpaste relieves subjective symptoms of dry month," Acta Odontol. Scand., Apr. 1998, 56(2):65-9.
Stewart et al., "Interdomain zinc site on human albumin," PNAS, 2003, 100(7):3701-3706.
Tian et al., "Using DGGE profiling to develop a novel culture medium suitable for oral microbial communities," Molecular Oral Microbiology, 2010, 25(5):357-367.
Twetman et al., 2003, "Caries-preventative effect of fluoride toothpaste a systematic review," Acta Odontol Scand., Dec. 2003, 61(6):347-55.
Wachi et al., "Antibacterial compsn. Zinc oxide—solubilized by amino acid, amino acid hydrochloride and/or amino acid alkali metal salt," Sep. 1982, vol. 1982(45).
Wallhausser et al., "Antimicrobial Preservatives in Europe: Experience with preservatives used in pharmaceuticals and cosmetics," Develop. Biol. Standard, 1974, 24:9-28.
Yao et al., "An investigtion of zirconium(IV)-glycine(CP-2) hybrid complex in bovine serum albumin protein matrix under varying conditions," J. of Materials Chemistry, 2011, 21:19005-19012.
Yousef et al., "In vitro antibacterial activity and minimum inhibitory concentration of zinc oxide and nano-particle zinc oxide against pathogenic strains," J. of Health Sciences. 2012, 2(4):38-42.
Zhu et al., "Synthesis and Crystal Structure of [Zn+{H2N(CH2)4CH(NH2)COONa}2SO4-] •H20," Chinese Science Bulletin, Sep. 1990, 35(18):1521-1525.
Corresponding Russian Office Action date Jul. 13, 2016.
Corresponding Chinese Search Report and Office Action dated Jul. 18, 2016.
Nockemann et al., "Task-specifie Ionic Liquid for solubilizing Metal Oxides," J. Phys. Chem. B, 2006, 110(42)20978-20992.
Rigano et al., "Buffering properties of trimethylglycine (Betaine) in cosmetics," SOFW Journal, 2003, 129:55-56, 58.

* cited by examiner

ORAL CARE PRODUCTS COMPRISING ZINC OXIDE AND TRIMETHYLGLYCINE

CROSS-REFERENCE TO RELATED APPLICATIONS

This application is a United States National Stage Application under 35 U.S.C. § 371 of International Application PCT/US2012/070537, filed on Dec. 19, 2012, the contents of which is hereby incorporated by reference in its entirety.

BACKGROUND

Dental erosion involves demineralization and damage to the tooth structure due to acid attack from nonbacterial sources. Erosion is found initially in the enamel and, if unchecked, may proceed to the underlying dentin. Dental erosion may be caused or exacerbated by acidic foods and drinks, exposure to chlorinated swimming pool water, and regurgitation of gastric acids. The tooth enamel is a negatively charged surface, which naturally tends to attract positively charged ions such as hydrogen and calcium ions, while resisting negatively charged ions such as fluoride ions. Depending upon relative pH of surrounding saliva, the tooth enamel will lose or gain positively charged ions such as calcium ions. Generally saliva has a pH between 7.2 to 7.4. When the pH is lowered and concentration of hydrogen ions becomes relatively high, the hydrogen ions will replace the calcium ions in the enamel, forming hydrogen phosphate (phosphoric acid), which damages the enamel and creates a porous, sponge-like roughened surface. If saliva remains acidic over an extended period, then remineralization may not occur, and the tooth will continue to lose minerals, causing the tooth to weaken and ultimately to lose structure.

Dentinal hypersensitivity is acute, localized tooth pain in response to physical stimulation of the dentine surface as by thermal (hot or cold) osmotic, tactile combination of thermal, osmotic and tactile stimulation of the exposed dentin. Exposure of the dentine, which is generally due to recession of the gums, or loss of enamel, frequently leads to hypersensitivity. Dentinal tubules open to the surface have a high correlation with dentine hypersensitivity. Dentinal tubules lead from the pulp to the cementum. When the surface cementum of the tooth root is eroded, the dentinal tubules become exposed to the external environment. The exposed dentinal tubules provide a pathway for transmission of fluid flow to the pulpal nerves, the transmission induced by changes in temperature, pressure and ionic gradients.

Heavy metal ions, such as zinc, are resistant to acid attack. Zinc ranks above hydrogen in the electrochemical series, so that metallic zinc in an acidic solution will react to liberate hydrogen gas as the zinc passes into solution to form di-cations, $Zn^{2+}$. Zinc has been shown to have antibacterial properties in plaque and caries studies.

Soluble zinc salts, such as zinc citrate, have been used in dentifrice compositions, see, e.g., U.S. Pat. No. 6,121,315, but have several disadvantages. Zinc ions in solution impart an unpleasant, astringent mouthfeel, so formulations that provide effective levels of zinc, and also have acceptable organoleptic properties, have been difficult to achieve. Finally, the zinc ions will react with anionic surfactants such as sodium lauryl sulfate, thus interfering with foaming and cleaning.

Zinc oxide has been used as an ingredient for toothpaste. While it has shown various oral care efficacies, its performance is constrained by the limited solubility of zinc oxide. Zinc oxide has a low solubility, about 0.16 mg per 100 ml of water at 30° C. Therefore, the zinc oxide that can be effectively delivered as soluble species is limited in quantity. Zinc oxide, delivered in conventional powder form, does not have a strong affinity toward dental or mucosal surface within the oral cavity. Therefore, the delivered zinc oxide will be washed away at the conclusion of the treatment period when the user spits out the toothpaste, mouthrinse, etc.

N,N,N-trimethylglycine (TMG or glycine betaine) possesses a quaternary ammonium structure. At neural pH, the compound exists as a zwitterion, forming an inner salt between the quaternary ammonium and the carboxy portions of the molecule. In the presence of strong acids, it will form acid addition salts, e.g., hydrochloride. The compound is originally isolated from sugar beets, and is used as a dietary supplement in animal feed and as a laboratory reagent stabilizer, e.g., in polymerase chain reactions. There are reports of its use in oral care products to treat dry mouth, e.g. U.S. Pat. No. 6,156,293, and in antiperspirant products, e.g. U.S. Pat. No. 6,969,510.

While the prior art discloses the use of various oral compositions for the treatment of dentinal hypersensitivity, dental caries, and enamel erosion and demineralization, there is still a need for additional compositions and methods which provide improved performance in such treatments.

SUMMARY

While zinc oxide is present with limited solubility in prior art formulations, it has now been discovered that zinc oxide can form a soluble complex with TMG in both its free form and acid addition form. When placed in formulation, this complex provides an effective concentration of zinc ions to the enamel and/or dentine surface, thereby protecting against erosion, reducing bacterial colonization and biofilm development, and providing enhanced shine to the teeth. Moreover, upon dilution during use, the formulation provides a precipitate which can plug the dentinal tubules, thereby reducing the sensitivity of the teeth. Further, upon dilution during use, the formulation provides a coating of solid material, primarily of zinc salts and some TMG on the dental surface. The strong affinity of the solid material to the dental surface allows for better substantivity, and permits controlled release of the actives therefrom. This is unexpected, at least partially because better solubilization is generally expected with dilution.

While providing efficient delivery of zinc in comparison to conventional formulations with zinc oxide, the formulations comprising zinc oxide and TMG do not exhibit the poor taste and mouthfeel, poor fluoride delivery, and poor foaming and cleaning associated with conventional zinc-based oral care products using soluble zinc salts.

The soluble complex formed from zinc oxide and TMG in its acid addition form is particularly effective. The acid can be any acid, preferably a hydrohalide. TMG in its acid addition form can be provided as one preexisting entity, such as TMG hydrochloride, or can be formed in situ by mixing TMG with the acid in various ratios, for example from 1:5 to 5:1 (moles of TMG versus moles of protons releaseable from the acid). The soluble complex formed from zinc oxide and TMG in its acid addition form can lead to precipitation upon dilution with water. The precipitates can be in the form of free-floating solids and/or be attached to dental and mucosal surfaces for subsequent release. In contrast, the soluble complex formed from zinc oxide and TMG in its free form is less capable of producing precipitation upon dilution with water.

The invention thus provides in one embodiment, a complex comprising zinc oxide and TMG in its free or acid addition form, for example a zinc-TMG-HCl complex, e.g., formed by combining zinc oxide and trimethylglycine hydrochloride in aqueous solution.

In a further embodiment, the invention provides oral care compositions, for example mouthwash, oral gel or dentifrice compositions, that comprise zinc oxide in combination with TMG in its free or acid addition form, e.g. that comprise a complex as described above. The compositions may optionally further comprise a fluoride source and or an additional phosphate source. The compositions may be formulated in a suitable oral care formulation e.g., a conventional dentifrice, oral gel or mouthwash base, e.g., comprising one or more abrasives, surfactants, foaming agents, vitamins, polymers, enzymes, humectants, thickeners, antimicrobial agents, preservatives, flavorings, and/or colorants.

The invention further provides methods of using the compositions of the invention to reduce and inhibit acid erosion of the enamel, clean the teeth, reduce bacterially-generated biofilm and plaque, reduce gingivitis, reduce oral malodor, provide relief from dry mouth, inhibit tooth decay and formation of cavities, and reduce dentinal hypersensitivity, comprising applying a composition of the invention to the teeth. The invention further provides methods of using the compositions of the invention to whiten the teeth by imparting a coating onto the teeth, wherein the coating is whiter than the native teeth.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

As used herein, "trimethylglycine" refers to N,N,N-trimethylglycine; and the terms may be used interchangeably herein.

The invention therefore provides, in a first embodiment, an oral care composition (Composition 1), comprising or prepared from a mixture of zinc oxide and trimethylglycine (TMG) in free or orally acceptable acid addition salt form; e.g., 1.1. Composition 1 wherein the level of zinc in the formulation by weight on an elemental basis is 0.05-4%, e.g., 1-2%, e.g., 0.5-1.5%, e.g., about 1%.
1.2. Composition 1 or 1.1 wherein the TMG is provided in orally acceptable acid addition salt form, e.g. hydrochloride salt form, or where TMG is formed in situ by providing TMG and acid (such as HCl) as separate entities in molar ratios between 1:5 to 5:1 (moles of TMG vs. moles of protons released from the acid).
1.3. Any of the foregoing compositions wherein the molar ratio of zinc oxide to TMG is from 1:1 to 1:10, e.g., about 1:5.
1.4. Any of the foregoing compositions wherein the molar ratio of zinc to TMG is from 5:1 to 1:2, e.g., about 1:1.
1.5. Any of the foregoing compositions wherein the pH is between pH 5 and pH 6.
1.6. Any of the foregoing compositions wherein the formulation includes the step of combining zinc oxide and trimethylglycine hydrochloride in aqueous solution.
1.7. Any of the foregoing compositions wherein the TMG is provided in hydrohalide salt form, and the zinc oxide and TMG form soluble complexes selected from zinc-TMG-halide complexes, zinc-halide complexes, and mixtures thereof, e.g. wherein the halide is selected from fluoride, chloride, bromide and mixtures thereof.
1.8. Any of the foregoing compositions wherein the TMG is provided in hydrohalide salt form, and the zinc oxide and TMG form two soluble complexes, one having the chemical composition $Zn_2O_8H_6X_2$ and the other having the chemical composition $Zn_2O_8H_5X_2$-TMG, wherein X is selected from Cl, F, Br, and mixtures thereof.
1.9. Any of the foregoing compositions wherein the TMG is provided in hydrochloride salt form, and the zinc oxide and TMG form soluble complexes selected from zinc-TMG-chloride complexes, zinc-chloride complexes, and mixtures thereof
1.10. Any of the foregoing compositions wherein the TMG is provided in hydrochloride salt form, and the zinc oxide and TMG form two soluble complexes, one having the chemical composition $Zn_2O_8H_6Cl_2$ and the other having the chemical composition $Zn_2O_8H_5Cl_2$-TMG.
1.11. Any of the foregoing compositions wherein a complex comprising zinc oxide and TMG is formed, in whole or in part, in situ after the composition is applied.
1.12. Any of the foregoing compositions wherein a complex comprising zinc oxide and TMG is formed, in whole or in part, in situ after the composition is formulated.
1.13. Any of the foregoing compositions comprising an acid, e.g., hydrochloric acid, e.g., such that the pH of the mixture is between 5 and 6.
1.14. Any of the foregoing compositions, further comprising a basic amino acid, e.g., lysine or arginine.
1.15. Any of the foregoing compositions, in a substantially anhydrous carrier, e.g. a carrier comprising less than 10% water.
1.16. Any of the foregoing compositions in the form of a toothpaste, gel, mouthwash, powder, cream, strip, or gum.
1.17. Any of the foregoing compositions in an orally acceptable base, e.g., a mouthwash, gel, or dentifrice base.
1.18. Any of the foregoing compositions in the form of a dentifrice, e.g., wherein the zinc oxide and TMG are present in an effective amount, e.g., in an amount of 0.05-4% zinc by weight, e.g., about 0.5-3%, e.g. about 1% zinc by weight, in a dentifrice base.
1.19. Composition 1.1, wherein the dentifrice base comprises an abrasive, e.g., an effective amount of a silica abrasive, e.g., 10-30%, e.g., about 20%.
1.20. Composition 1 in the form of a mouthwash, e.g., wherein the zinc oxide is present in an effective amount, e.g., in an amount of 0.05-4% of zinc by weight, e.g., about 1% of zinc by weight.
1.21. Any of the foregoing compositions further comprising an effective amount of a fluoride ion source, e.g., providing 500 to 3000 ppm fluoride.
1.22. Any of the foregoing compositions further comprising an effective amount of fluoride, e.g., wherein the fluoride is a salt selected from stannous fluoride, sodium fluoride, potassium fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, and combinations thereof.

1.23. Any of the preceding compositions comprising an effective amount of one or more alkali phosphate salts, e.g., sodium, potassium or calcium salts, e.g., selected from alkali dibasic phosphate and alkali pyrophosphate salts, e.g., alkali phosphate salts selected from sodium phosphate dibasic, potassium phosphate dibasic, dicalcium phosphate dihydrate, calcium pyrophosphate, tetrasodium pyrophosphate, tetrapotassium pyrophosphate, sodium tripolyphosphate, and mixtures of any of two or more of these, e.g., in an amount of 1-20%, e.g., 2-8%, e.g., ca. 5%, by weight of the composition.

1.24. Any of the foregoing compositions comprising buffering agents, e.g., sodium phosphate buffer (e.g., sodium phosphate monobasic and disodium phosphate).

1.25. Any of the foregoing compositions comprising a humectant, e.g., selected from glycerin, sorbitol, propylene glycol, polyethylene glycol, xylitol, and mixtures thereof, e.g. comprising at least 20%, e.g., 20-40%, e.g., 25-35% glycerin.

1.26. Any of the preceding compositions comprising one or more surfactants, e.g., selected from anionic, cationic, zwitterionic, and nonionic surfactants, and mixtures thereof, e.g., comprising an anionic surfactant, e.g., a surfactant selected from sodium lauryl sulfate, sodium ether lauryl sulfate, and mixtures thereof, e.g. in an amount of from about 0.3% to about 4.5% by weight, e.g. 1-2% sodium lauryl sulfate (SLS); and/or a zwitterionic surfactant, for example a betaine surfactant, for example cocamidopropylbetaine, e.g. in an amount of from about 0.1% to about 4.5% by weight, e.g. 0.5-2% cocamidopropylbetaine.

1.27. Any of the preceding compositions further comprising a viscosity modifying amount of one or more of polysaccharide gums, for example xanthan gum or carrageenan, silica thickener, and combinations thereof 1.28. Any of the preceding compositions comprising gum strips or fragments.

1.29. Any of the preceding compositions further comprising flavoring, fragrance and/or coloring.

1.30. Any of the foregoing compositions comprising an effective amount of one or more antibacterial agents, for example comprising an antibacterial agent selected from halogenated diphenyl ether (e.g. triclosan), herbal extracts and essential oils (e.g., rosemary extract, tea extract, magnolia extract, thymol, menthol, eucalyptol, geraniol, carvacrol, citral, hinokitol, catechol, methyl salicylate, epigallocatechin gallate, epigallocatechin, gallic acid, miswak extract, sea-buckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, metal ions (e.g., zinc salts, for example, zinc citrate, stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts; and mixtures of any of the foregoing; e.g., comprising triclosan or cetylpyridinium chloride.

1.31. Any of the foregoing compositions comprising an antibacterially effective amount of triclosan, e.g. 0.1-0.5%, e.g. about 0.3%.

1.32. Any of the preceding compositions further comprising a whitening agent, e.g., a selected from the group consisting of peroxides, metal chlorites, perborates, percarbonates, peroxyacids, hypochlorites, and combinations thereof.

1.33. Any of the preceding compositions further comprising hydrogen peroxide or a hydrogen peroxide source, e.g., urea peroxide or a peroxide salt or complex (e.g., such as peroxyphosphate, peroxycarbonate, perborate, peroxysilicate, or persulphate salts; for example calcium peroxyphosphate, sodium perborate, sodium carbonate peroxide, sodium peroxyphosphate, and potassium persulfate);

1.34. Any of the preceding compositions further comprising an agent that interferes with or prevents bacterial attachment, e.g., solbrol or chitosan.

1.35. Any of the preceding compositions further comprising a source of calcium and phosphate selected from (i) calcium-glass complexes, e.g., calcium sodium phosphosilicates, and (ii) calcium-protein complexes, e.g., casein phosphopeptide-amorphous calcium phosphate 1.36. Any of the preceding compositions further comprising a soluble calcium salt, e.g., selected from calcium sulfate, calcium chloride, calcium nitrate, calcium acetate, calcium lactate, and combinations thereof 1.37. Any of the preceding compositions further comprising a physiologically or orally acceptable potassium salt, e.g., potassium nitrate or potassium chloride, in an amount effective to reduce dentinal sensitivity.

1.38. Any of the foregoing compositions further comprising an anionic polymer, e.g., a synthetic anionic polymeric polycarboxylate, e.g., wherein the anionic polymer is selected from 1:4 to 4:1 copolymers of maleic anhydride or acid with another polymerizable ethylenically unsaturated monomer; e.g., wherein the anionic polymer is a methyl vinyl ether/maleic anhydride (PVM/MA) copolymer having an average molecular weight (M.W.) of about 30,000 to about 1,000,000, e.g. about 300,000 to about 800,000, e.g., wherein the anionic polymer is about 1-5%, e.g., about 2%, of the weight of the composition.

1.39. Any of the preceding compositions further comprising a breath freshener, fragrance or flavoring.

1.40. Any of the forgoing compositions for use to reduce and inhibit acid erosion of the enamel, clean the teeth, reduce bacterially-generated biofilm and plaque, reduce gingivitis, inhibit tooth decay and formation of cavities, and reduce dentinal hypersensitivity.

1.41. Any of the foregoing compositions produced by a process comprising the step of mixing zinc oxide and trimethylglycine hydrochloride in aqueous media.

1.42. Any of the foregoing compositions wherein upon dilution with water, e.g., to a level of 1% of less of zinc relative to water, a zinc precipitate is formed.

The invention further provides methods to reduce and inhibit acid erosion of the enamel, clean the teeth, reduce bacterially-generated biofilm and plaque, reduce gingivitis, provide relief from dry mouth, reduce oral malodor, inhibit tooth decay and formation of cavities, improve whiteness, and reduce dentinal hypersensitivity, comprising applying an effective amount of a composition of the invention, e.g., any of Composition 1, et seq. to the teeth.

The invention further provides a method of making a composition comprising zinc oxide and TMG, e.g., any of Composition 1, et seq. comprising the step of combining zinc oxide and an orally acceptable acid addition salt of TMG, e.g., TMG-HCl, in an aqueous medium.

For example, in various embodiments, the invention provides methods to (i) reduce hypersensitivity of the teeth, (ii) to reduce plaque accumulation, (iii) reduce or inhibit demineralization and promote remineralization of the teeth, (iv) inhibit microbial biofilm formation in the oral cavity, (v) reduce or inhibit gingivitis, (vi) promote healing of sores or cuts in the mouth, (vii) reduce levels of acid producing bacteria, (viii) to increase relative levels of non-cariogenic and/or non-plaque forming bacteria, (ix) reduce or inhibit formation of dental caries, (x), reduce, repair or inhibit pre-carious lesions of the enamel, e.g., as detected by quantitative light-induced fluorescence (QLF) or electrical caries measurement (ECM), (xi) treat, relieve or reduce dry mouth, (xii) clean the teeth and oral cavity, (xiii) reduce erosion, (xiv) whiten teeth; (xv) reduce tartar build-up, (xvi) reduce oral malodor, and/or (xvii) promote systemic health, including cardiovascular health, e.g., by reducing potential for systemic infection via the oral tissues, comprising applying any of Compositions 1, et seq. as described above to the oral cavity of a person in need thereof, e.g., one or more times per day. The invention further provides Compositions 1, et seq. for use in any of these methods.

The invention further provides the use of zinc oxide and TMG in free or orally acceptable salt form, e.g., trimethylglycine hydrochloride, to make an oral care composition, e.g. any of Compositions 1, et. seq.

In some embodiments, the compositions of the present invention provide relief from dentinal sensitivity after 5 seconds. In some embodiments, the compositions of the present invention provide relief from dentinal sensitivity after 10 seconds. In some embodiments, the compositions of the present invention provide relief from dentinal sensitivity after 15 seconds. In some embodiments, the compositions of the present invention provide relief from dentinal sensitivity after 30 seconds. In some embodiments, the compositions of the present invention provide relief from dentinal sensitivity after 60 seconds.

The invention further provides the use of zinc oxide together with TMG in free or orally acceptable salt form (i.e., the acid addition form) to reduce and inhibit acid erosion of the enamel, clean the teeth, reduce bacterially-generated biofilm and plaque, reduce gingivitis, inhibit tooth decay and formation of cavities, and reduce dentinal hypersensitivity; (ii) the use of a zinc amino acid halide precursors selected from (a) zinc oxide and an amino acid halide, and/or (b) zinc oxide, an amino acid and optionally halogen acid in the manufacture of a composition to reduce and inhibit acid erosion of the enamel, clean the teeth, reduce bacterially-generated biofilm and plaque, reduce gingivitis, reduce oral malodor, provide relief from dry mouth, inhibit tooth decay and formation of cavities, and reduce dentinal hypersensitivity.

It is discovered that the interaction of the zinc and the TMG converts zinc oxide to a highly soluble complex. Preferably, the TMG is in acid addition salt form, e.g. hydrochloride form. The complex is highly soluble at concentrations in water, e.g., levels corresponding to about 1% or more of zinc. But with increasing dilution in water, e.g., at concentrations of 0.1 to 1%, e.g. about 0.5%, of zinc in water, the complex disassociates, and the zinc ion in the complex reverts to insoluble forms, which is substantially free from zinc oxide. In experiments wherein complexes are formed using zinc oxide and an amino acid such as lysine, precipitation upon dilution is also observed, but the precipitate is zinc oxide, so the formation of a precipitate substantially free from zinc oxide is unexpected.

Without wishing to be bound by the theory, it is noted that at least two kinds of complexes exist in solution. At least one complex is derived from zinc without interaction with TMG, and at least one complex is derived from zinc in interaction with TMG. One complex has the structure of $Zn_2O_8H_5Cl_2$, and the other has the structure of $Zn_2O_8H_5Cl_2$-TMG.

This dynamic—reduced solubility upon increasing dilution—is unusual and unexpected. The dilution upon brushing or rinsing or combination with saliva facilitates the deposition of the zinc precipitate on the teeth with administration, which acts to occlude the dentinal tubules, thereby reducing hypersensitivity, and also providing zinc to the enamel, which reduces acid erosion, biofilm and plaque formation.

It will be understood that although the zinc and TMG may be primarily in the form of precursor materials (e.g. zinc oxide and TMG-HCl) or in the form of a complex, there may be some degree of equilibrium, so that the proportion of material which is actually in complex compared to the proportion in precursor form may vary depending on the precise conditions of formulation, concentration of materials, pH, presence or absence of water, presence or absence of other charged molecules, and so forth.

It will be understood that the complex can be in the form of a mixture as well. Zinc oxide and TMG may form one type of complex, while zinc oxide and TMG in an acid addition form may form another. These complexes may be present in different ratios, particularly when TMG and the protons from the acid are provided in unequal molar amounts.

The actives can be delivered in the form of any oral care formulations, for example a toothpaste, gel, mouthwash, powder, cream, strip, gum, or any other known in the art.

If the actives are delivered in the form of a mouthwash, a person desiring the benefits rinses with the stock solution and natural dilution of the stock solution by saliva will initiate the precipitation of the zinc. Alternatively, the person can mix a stock solution with an appropriate amount of an aqueous diluent (e.g. to provide a concentration of zinc relative to water of about 0.1-1%), and rinse with the mixture.

In another embodiment, the mixture is prepared and immediately transferred into a retaining tray, such as those used in holding whitening gels, and the person can wear the tray for the effective period of time. The teeth that are in contact with the mixture will be treated. For use with retaining tray, the mixture can be in the form of a low-viscosity liquid or a gel.

In another embodiment, the stock solution, or a mixture of stock solution with water, is applied to the teeth in a gel formulation, e.g., wherein the gel can stay on the tooth for an extended period of time for effective treatment.

In another embodiment, the active is provided in a toothpaste. Upon brushing, the active is diluted by saliva and water, leading to precipitation and the formation of deposits and occluding particles.

The rate of precipitation from the formulation can be modulated by adjusting concentration of the complex in the stock solution, and changing the ratio of the stock to water.

A more diluted formula leads to faster precipitation and is thus preferred when a fast treatment is desired.

The benefits of the oral care compositions of the invention are numerous. By providing zinc ions and zinc containing compounds that can release zinc ions in oral cavities, the oral care compositions of the invention provide antimicrobial, antiplaque, antigingivitis, anti-malodor, anticaries, and anticalculus benefits. The occluding particles and the surface deposits are compounds containing zinc salts which can release zinc ions into oral cavities and provide the various benefits as recognized above. The coating formed on dental surfaces due to deposition can enhance the whiteness of the dental surface, thus providing whitening benefits. Additional benefits include but are not limited to anti-attachment, anti-periodontitis and anti-bone loss, as well as promotion of wound healing.

A second benefit is the antierosive properties of zinc ions, which form antierosive deposits on tooth surfaces through oxidation and hydrolysis. The surface deposits, as well as the occluding particles, can react with and neutralize acids, thus protecting the dental surface from the erosive effects of the acids. It is also noted that when the surface deposits and occluding particles neutralize acids, beneficial zinc ions can be released, providing oral care benefits other than anti-erosion.

A third benefit is anti-sensitivity benefit as a result of the occlusion. Occlusion of dentin tubules leads to sensitivity relief.

A fourth benefit is the benefit associated with the TMG. The TMG, due to its zwitterionic character, provides a buffering effect, counteracting the acid which can damage the teeth and so can provide anticaries benefits. In addition, TMG has been recognized to provide relief from dry-mouth.

In a particular embodiment, the invention provides an ionic complex comprising zinc oxide, TMG and an anionic species, e.g. a halide, for example chloride. In a particular embodiment, the invention provides a complex formed by combining zinc oxide and TMG HCl in an aqueous media to form a complex conveniently referred to as a ZnO-TMG HCl complex.

In another embodiment, the invention provides oral care formulations comprising a ZnO-TMG HCl complex, e.g., compositions according to Composition 1, et seq., comprising a ZnO-TMG HCl complex e.g. in the form of a mouthrinse, a gel, a toothpaste, a cream, a powder, a strip, or a gum.

In one embodiment, if the desired formulation is in the form of a mouthrinse, a two-component delivery system is contemplated. The first component is a concentrated solution of the ZnO-TMG HCl complex, and the second component is substantially water. The two components are mixed by the administrator/user immediately before treatment. Alternatively, a single-component delivery system in the form of a mouthrinse is contemplated, where the system comprises a concentrated solution of the ZnO-TMG HCl complex and the diluent is supplied by the administrator/user either in the form of water naturally involved in a typical oral care treatment and/or saliva generated by the user.

The invention is also directed, in further embodiments, to a controlled release system and a method for delivering zinc ions and TMG over an extended period of time within oral cavities, comprising administering a composition according to Composition 1, et seq.

In particular embodiments, Compositions 1, et seq. provide complexes from zinc oxide and TMG, for example zinc-TMG-chloride complexes, and/or the zinc oxide and TMG in free or acid addition salt form, e.g., TMG-HCl, as complex precursors, which can react in situ with water to form the complexes. The in situ formation provides ease of formulation. In another embodiment, the water permitting formation of the complex from the precursor comes from saliva and/or rinsing water that comes into contact with the composition after application.

In a particular embodiment, the TMG is provided in the form of an acid addition salt, for example a hydrohalide, e.g. trimethylglycine hydrochloride, which forms a complex of complexes in aqueous media with zinc oxide.

Because the number of moles or weight percent of various zinc salts and complexes herein will vary based on the particular salt or complex form, we frequently refer herein to the amount of total zinc in the formulation by weight or by molar amount, irrespective of its salt or complex form. In some embodiments, the total amount of zinc in the composition is 0.05 to 8% by weight of the composition. In other embodiments, the total amount of zinc is at least 0.1, at least 0.2, at least 0.3, at least 0.4, at least 0.5, or at least 1 up to 8% by weight of the composition. In other embodiments, the total amount of zinc in the composition is less than 5, less than 4, less than 3, less than 2, or less than 1 to 0.05% by weight of the composition. For example, in some embodiments, the total amount of zinc in the composition may be about 1%.

Active Agents:

The compositions of the invention may comprise various agents which are active to protect and enhance the strength and integrity of the enamel and tooth structure and/or to reduce bacteria and associated tooth decay and/or gum disease, including or in addition to the zinc—TMG—halide complexes. Effective concentration of the active ingredients used herein will depend on the particular agent and the delivery system used. It is understood that a toothpaste for example will typically be diluted with water upon use, while a mouth rinse typically will not be. Thus, an effective concentration of active in a toothpaste will ordinarily be 5-15× higher than required for a mouth rinse. The concentration will also depend on the exact salt or polymer selected. For example, where the active agent is provided in salt form, the counterion will affect the weight of the salt, so that if the counterion is heavier, more salt by weight will be required to provide the same concentration of active ion in the final product. Arginine, where present, may be present at levels from, e.g., about 0.1 to about 20 wt % (expressed as weight of free base), e.g., about 1 to about 10 wt % for a consumer toothpaste or about 7 to about 20 wt % for a professional or prescription treatment product. Fluoride where present may be present at levels of, e.g., about 25 to about 25,000 ppm, for example about 750 to about 2,000 ppm for a consumer toothpaste, or about 2,000 to about 25,000 ppm for a professional or prescription treatment product. Levels of antibacterial agents will vary similarly, with levels used in toothpaste being e.g., about 5 to about 15 times greater than used in mouthrinse. For example, a triclosan toothpaste may contain about 0.3 wt % triclosan.

Fluoride Ion Source:

The oral care compositions may further include one or more fluoride ion sources, e.g., soluble fluoride salts. A wide variety of fluoride ion-yielding materials can be employed as sources of soluble fluoride in the present compositions. Examples of suitable fluoride ion-yielding materials are found in U.S. Pat. No. 3,535,421, to Briner et al.; U.S. Pat. No. 4,885,155, to Parran, Jr. et al. and U.S. Pat. No. 3,678,154, to Widder et al. Representative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, sodium monofluorophosphate as well as mixtures thereof. In certain embodiments, the oral care composition of the invention may also contain a source of fluoride ions or fluorine-providing ingredient in amounts sufficient to supply about 25 ppm to about 25,000 ppm of fluoride ions, generally at least about 500 ppm, e.g., about 500 to about 2000 ppm, e.g., about 1000 to about 1600 ppm, e.g., about 1450 ppm. The appropriate level of fluoride will depend on the particular application. A toothpaste for general consumer use would typically have about 1000 to about 1500 ppm, with pediatric toothpaste having somewhat less. A dentifrice or coating for professional application could have as much as about 5,000 or even about 25,000 ppm fluoride. Fluoride ion sources may be added to the compositions of the invention at a level of about 0.01 wt. % to about 10 wt. % in one embodiment or about 0.03 wt. % to about 5 wt. %, and in another embodiment about 0.1 wt. % to about 1 wt. % by weight of the composition in another embodiment. Weights of fluoride salts to provide the appropriate level of fluoride ion will obviously vary based on the weight of the counterion in the salt.

In various embodiments, the amino acid is present in an amount of about 0.5 wt. % to about 20 wt. % of the total composition weight, about 0.5 wt. % to about 10 wt. % of the total composition weight, for example about 1.5 wt. %, about 3.75 wt. %, about 5 wt. %, or about 7.5 wt. % of the total composition weight in the case of a dentifrice, or for example about 0.5-2 wt. %, e.g., about 1% in the case of a mouthwash.

Abrasives:

The compositions of the invention, e.g. Composition 1 et seq. include silica abrasives, and may comprise additional abrasives, e.g., a calcium phosphate abrasive, e.g., tricalcium phosphate ($Ca_3(PO_4)_2$), hydroxyapatite ($Ca_{10}(PO_4)_6(OH)_2$), or dicalcium phosphate dihydrate ($CaHPO_4 \cdot 2H_2O$, also sometimes referred to herein as DiCal) or calcium pyrophosphate; calcium carbonate abrasive; or abrasives such as sodium metaphosphate, potassium metaphosphate, aluminum silicate, calcined alumina, bentonite or other siliceous materials, or combinations thereof.

Other silica abrasive polishing materials useful herein, as well as the other abrasives, generally have an average particle size ranging between about 0.1 and about 30 microns, about between 5 and about 15 microns. The silica abrasives can be from precipitated silica or silica gels, such as the silica xerogels described in U.S. Pat. No. 3,538,230, to Pader et al. and U.S. Pat. No. 3,862,307, to Digiulio. Particular silica xerogels are marketed under the trade name Syloid® by the W. R. Grace & Co., Davison Chemical Division. The precipitated silica materials include those marketed by the J. M. Huber Corp. under the trade name Zeodent®, including the silica carrying the designation Zeodent 115 and 119. These silica abrasives are described in U.S. Pat. No. 4,340,583, to Wason. In certain embodiments, abrasive materials useful in the practice of the oral care compositions in accordance with the invention include silica gels and precipitated amorphous silica having an oil absorption value of less than about 100 cc/100 g silica and in the range of about 45 cc/100 g to about 70 cc/100 g silica. Oil absorption values are measured using the ASTA Rub-Out Method D281. In certain embodiments, the silicas are colloidal particles having an average particle size of about 3 microns to about 12 microns, and about 5 to about 10 microns. Low oil absorption silica abrasives particularly useful in the practice of the invention are marketed under the trade designation Sylodent XWA® by Davison Chemical Division of W.R. Grace & Co., Baltimore, Md. 21203. Sylodent 650 XWA®, a silica hydrogel composed of particles of colloidal silica having a water content of 29% by weight averaging about 7 to about 10 microns in diameter, and an oil absorption of less than about 70 cc/100 g of silica is an example of a low oil absorption silica abrasive useful in the practice of the present invention.

Foaming Agents:

The oral care compositions of the invention also may include an agent to increase the amount of foam that is produced when the oral cavity is brushed. Illustrative examples of agents that increase the amount of foam include, but are not limited to polyoxyethylene and certain polymers including, but not limited to, alginate polymers. The polyoxyethylene may increase the amount of foam and the thickness of the foam generated by the oral care carrier component of the present invention. Polyoxyethylene is also commonly known as polyethylene glycol ("PEG") or polyethylene oxide. The polyoxyethylenes suitable for this invention will have a molecular weight of about 200,000 to about 7,000,000. In one embodiment the molecular weight will be about 600,000 to about 2,000,000 and in another embodiment about 800,000 to about 1,000,000. Polyox® is the trade name for the high molecular weight polyoxyethylene produced by Union Carbide. The polyoxyethylene may be present in an amount of about 1% to about 90%, in one embodiment about 5% to about 50% and in another embodiment about 10% to about 20% by weight of the oral care carrier component of the oral care compositions of the present invention. Where present, the amount of foaming agent in the oral care composition (i.e., a single dose) is about 0.01 to about 0.9% by weight, about 0.05 to about 0.5% by weight, and in another embodiment about 0.1 to about 0.2% by weight.

Surfactants:

The compositions useful in the invention may contain anionic surfactants, for example:

i. water-soluble salts of higher fatty acid monoglyceride monosulfates, such as the sodium salt of the monosulfated monoglyceride of hydrogenated coconut oil fatty acids such as sodium N-methyl N-cocoyl taurate, sodium cocomonoglyceride sulfate, ii. higher alkyl sulfates, such as sodium lauryl sulfate, iii. higher alkyl-ether sulfates, e.g., of formula $CH_3(CH_2)_mCH_2(OCH_2CH_2)_nOSO_3X$, wherein m is 6-16, e.g., 10, n is 1-6, e.g., 2, 3 or 4, and X is Na or K, for example sodium laureth-2 sulfate ($CH_3(CH_2)_{10}CH_2(OCH_2CH_2)_2OSO_3Na$).

iv. higher alkyl aryl sulfonates such as sodium dodecyl benzene sulfonate (sodium lauryl benzene sulfonate)

v. higher alkyl sulfoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate.

By "higher alkyl" is meant, e.g., $C_{6-30}$ alkyl. In particular embodiments, the anionic surfactant is selected from sodium lauryl sulfate and sodium ether lauryl sulfate. The anionic surfactant may be present in an amount which is effective, e.g., >0.01% by weight of the formulation, but not at a concentration which would be irritating to the oral tissue, e.g., <10%, and optimal concentrations depend on the particular formulation and the particular surfactant. For example, concentrations used or a mouthwash are typically on the order of one tenth that used for a toothpaste. In one embodiment, the anionic surfactant is present in a toothpaste at from about 0.3% to about 4.5% by weight, e.g., about 1.5%. The compositions of the invention may optionally contain mixtures of surfactants, e.g., comprising anionic surfactants and other surfactants that may be anionic, cationic, zwitterionic or nonionic. Generally, surfactants are those which are reasonably stable throughout a wide pH range. Surfactants are described more fully, for example, in U.S. Pat. No. 3,959,458, to Agricola et al.; U.S. Pat. No. 3,937,807, to Haefele; and U.S. Pat. No. 4,051,234, to Gieske et al. In certain embodiments, the anionic surfactants useful herein include the water-soluble salts of alkyl sulfates having about 10 to about 18 carbon atoms in the alkyl radical and the water-soluble salts of sulfonated monoglycerides of fatty acids having about 10 to about 18 carbon atoms. Sodium lauryl sulfate, sodium lauroyl sarcosinate and sodium coconut monoglyceride sulfonates are examples of anionic surfactants of this type. In a particular embodiment, the composition of the invention, e.g., Composition 1, et seq., comprises sodium lauryl sulfate.

The surfactant or mixtures of compatible surfactants can be present in the compositions of the present invention in about 0.1% to about 5.0%, in another embodiment about 0.3% to about 3.0% and in another embodiment about 0.5% to about 2.0% by weight of the total composition.

Tartar Control Agents:

In various embodiments of the present invention, the compositions comprise an anticalculus (tartar control) agent. Suitable anticalculus agents include without limitation phosphates and polyphosphates (for example pyrophosphates), polyaminopropanesulfonic acid (AMPS), hexametaphosphate salts, zinc citrate trihydrate, polypeptides, polyolefin sulfonates, polyolefin phosphates, diphosphonates. The invention thus may comprise phosphate salts. In particular embodiments, these salts are alkali phosphate salts, i.e., salts of alkali metal hydroxides or alkaline earth hydroxides, for example, sodium, potassium or calcium salts. "Phosphate" as used herein encompasses orally acceptable mono- and polyphosphates, for example, $P_{1-6}$ phosphates, for example monomeric phosphates such as monobasic, dibasic or tribasic phosphate; dimeric phosphates such as pyrophosphates; and multimeric phosphates, e.g., sodium hexametaphosphate. In particular examples, the selected phosphate is selected from alkali dibasic phosphate and alkali pyrophosphate salts, e.g., selected from sodium phosphate dibasic, potassium phosphate dibasic, dicalcium phosphate dihydrate, calcium pyrophosphate, tetrasodium pyrophosphate, tetrapotassium pyrophosphate, sodium tripolyphosphate, and mixtures of any of two or more of these. In a particular embodiment, for example the compositions comprise a mixture of tetrasodium pyrophosphate ($Na_4P_2O_7$), calcium pyrophosphate ($Ca_2P_2O_7$), and sodium phosphate dibasic ($Na_2HPO_4$), e.g., in amounts of ca. 3-4% of the sodium phosphate dibasic and ca. 0.2-1% of each of the pyrophosphates. In another embodiment, the compositions comprise a mixture of tetrasodium pyrophosphate (TSPP) and sodium tripolyphosphate (STPP)($Na_5P_3O_{10}$), e.g., in proportions of TSPP at about 1-2% and STPP at about 7% to about 10%. Such phosphates are provided in an amount effective to reduce erosion of the enamel, to aid in cleaning the teeth, and/or to reduce tartar buildup on the teeth, for example in an amount of 2-20%, e.g., ca. 5-15%, by weight of the composition.

Flavoring Agents:

The oral care compositions of the invention may also include a flavoring agent. Flavoring agents which are used in the practice of the present invention include, but are not limited to, essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Certain embodiments employ the oils of peppermint and spearmint. The flavoring agent may be incorporated in the oral composition at a concentration of about 0.1 to about 5% by weight e.g. about 0.5 to about 1.5% by weight.

Polymers:

The oral care compositions of the invention may also include additional polymers to adjust the viscosity of the formulation or enhance the solubility of other ingredients. Such additional polymers include polyethylene glycols, polysaccharides (e.g., cellulose derivatives, for example carboxymethyl cellulose, or polysaccharide gums, for example xanthan gum or carrageenan gum). Acidic polymers, for example polyacrylate gels, may be provided in the form of their free acids or partially or fully neutralized water soluble alkali metal (e.g., potassium and sodium) or ammonium salts.

Silica thickeners, which form polymeric structures or gels in aqueous media, may be present. Note that these silica thickeners are physically and functionally distinct from the particulate silica abrasives also present in the compositions, as the silica thickeners are very finely divided and provide little or no abrasive action. Other thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as karaya, gum arabic, and gum tragacanth can also be incorporated. Colloidal magnesium aluminum silicate can also be used as component of the thickening composition to further improve the composition's texture. In certain embodiments, thickening agents in an amount of about 0.5% to about 5.0% by weight of the total composition are used.

The compositions of the invention may include an anionic polymer, for example in an amount of from about 0.05 to about 5%. Such agents are known generally for use in dentifrice, although not for this particular application, useful in the present invention are disclosed in U.S. Pat. Nos. 5,188,821 and 5,192,531; and include synthetic anionic polymeric polycarboxylates, such as 1:4 to 4:1 copolymers of maleic anhydride or acid with another polymerizable ethylenically unsaturated monomer, preferably methyl vinyl ether/maleic anhydride having a molecular weight (M.W.) of about 30,000 to about 1,000,000, most preferably about 300,000 to about 800,000. These copolymers are available for example as Gantrez. e.g., AN 139 (M.W. 500,000), AN 119 (M.W. 250,000) and preferably S-97 Pharmaceutical Grade (M.W. 700,000) available from ISP Technologies, Inc., Bound Brook, N.J. 08805. The enhancing agents when present are present in amounts ranging from about 0.05 to about 3% by weight. Other operative polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone. Suitable generally, are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility. A further class of polymeric agents includes a composition containing homopolymers of substituted acrylamides and/or homopolymers of unsaturated sulfonic acids and salts thereof, in particular where polymers are based on unsaturated sulfonic acids selected from acrylamidoalykane sulfonic acids such as 2-acrylamide 2 methylpropane sulfonic acid having a molecular weight of 1,000 to about 2,000,000, described in U.S. Pat. No. 4,842,847, Jun. 27, 1989 to Zahid. Another useful class of polymeric agents includes polyamino acids containing proportions of anionic surface-active amino acids such as aspartic acid, glutamic acid and phosphoserine, e.g. as disclosed in U.S. Pat. No. 4,866,161 Sikes et al.

Water:

The oral compositions may comprise significant levels of water. Water employed in the preparation of commercial oral compositions should be deionized and free of organic impurities. The amount of water in the compositions includes the free water which is added plus that amount which is introduced with other materials.

Humectants:

Within certain embodiments of the oral compositions, it is also desirable to incorporate a humectant to prevent the composition from hardening upon exposure to air. Certain humectants can also impart desirable sweetness or flavor to dentifrice compositions. Suitable humectants include edible polyhydric alcohols such as glycerine, sorbitol, xylitol, propylene glycol as well as other polyols and mixtures of these humectants. In one embodiment of the invention, the principal humectant is glycerin, which may be present at levels of greater than 25%, e.g. 25-35% about 30%, with 5% or less of other humectants.

Other Optional Ingredients:

In addition to the above-described components, the embodiments of this invention can contain a variety of optional dentifrice ingredients some of which are described below. Optional ingredients include, for example, but are not limited to, adhesives, sudsing agents, flavoring agents, sweetening agents, additional antiplaque agents, abrasives, and coloring agents. These and other optional components are further described in U.S. Pat. No. 5,004,597, to Majeti; U.S. Pat. No. 3,959,458 to Agricola et al. and U.S. Pat. No. 3,937,807, to Haefele, all being incorporated herein by reference.

Unless stated otherwise, all percentages of composition components given in this specification are by weight based on a total composition or formulation weight of 100%.

Unless otherwise specifically identified, the ingredients for use in the compositions and formulations of the present invention are preferably cosmetically acceptable ingredients. By "cosmetically acceptable" is meant suitable for use in a formulation for topical application to human skin. A cosmetically acceptable excipient, for example, is an excipient which is suitable for external application in the amounts and concentrations contemplated in the formulations of this invention, and includes for example excipients which are "Generally Recognized as Safe" (GRAS) by the United States Food and Drug Administration.

The compositions and formulations as provided herein are described and claimed with reference to their ingredients, as is usual in the art. As would be evident to one skilled in the art, the ingredients may in some instances react with one another, so that the true composition of the final formulation may not correspond exactly to the ingredients listed. Thus, it should be understood that the invention extends to the product of the combination of the listed ingredients.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

EXAMPLES

Example 1

Sample 1, ZnO-TMG, is prepared as follows. At room temperature, 50 mL of deionized water is slowly added to a flask containing 4.0712 g (0.05003 mol) of zinc oxide powder, and 5.8595 g (0.05002 mole) of TMG in its free form (CAS#107-43-7). The mixture is stirred overnight for about 20 hours. Unreacted zinc oxide is removed by centrifuging followed by filtering through a 0.45 micron membrane. The final product is a transparent solution.

TABLE 1

| SAMPLE 1 | ZnO | TMG |
| --- | --- | --- |
| Amount added | 4.0712 g, 0.05003 mol | 5.8595 g, 0.05002 mole |
| pH of final solution | | 7.77 |

Sample 2, ZnO-TMG-HCl, is prepared as follows. At room temperature, 50 mL of deionized water is slowly added to a flask containing 4.0712 g (0.05003 mol) of zinc oxide powder, and 7.6832 g (0.05002 mole) of TMG-HCl (CAS#590-46-5). The mixture is stirred overnight for about 20 hours. Unreacted zinc oxide is removed by centrifuging followed by filtering through a 0.45 micron membrane. The final product is a transparent solution.

TABLE 2

| SAMPLE 2 | ZnO | TMG-HCl |
| --- | --- | --- |
| Amount added | 4.0712 g, 0.05003 mol | 7.6832 g, 0.05002 mole |
| pH of final solution | | 6.02 |

Sample 3, ZnO-TMG-HCl, is prepared as follows. 1M TMG-HCl solution is prepared by dissolving 7.68 g (0.0500 mole) of TMG-HCl (CAS#590-46-5) in 50 mL of deionized water. At room temperature, 4.07 g (0.0500 mol) of zinc oxide powder is slowly added to the TMG-HCl solution. The mixture is stirred overnight for about 20 hours. Unreacted zinc oxide is removed by centrifuging followed by filtering through a 0.45 micron membrane. The final product is a transparent solution.

TABLE 3

| SAMPLE 3 | ZnO | TMG-HCl |
|---|---|---|
| Amount added | 4.07 g, 0.0500 mol | 7.68 g, 0.0500 mole |
| pH of final solution | | 5.56 |

Each sample is evaluated for its ability and rate to form precipitation or flocculation upon dilution. For this analysis, samples with various dilution ratios (for example, 2× through 32×) are prepared and kept at 37° C. The samples are monitored periodically and their efficiency of generating precipitation/flocculation are recorded.

Dilutions experiments indicate that ZnO-TMG-HCl (samples 2 and 3) generates precipitation/flocculation, and thus is preferred for depositing solid particles on dentine surface. Rate of flocculation/precipitation depends on the dilution ratio, which is related to the initial zinc concentration at the time water is mixed with the stock solutions in desired proportions.

A first dilution experiment is carried out using ZnO-TMG-HCl sample 2. Dilutions are prepared by mixing the stock solution with water in different ratios based on volume, producing samples with 2× (1:1 stock and water), 4×, 8×, 16× and 32× dilutions. The diluted samples are kept at 37° C., and the rates at which flocculation/precipitation occurred are monitored. One hour from mixing, visible precipitations are observed in systems with 2×, 4× and 8× dilutions.

A second dilution experiment is carried out using ZnO-TMG-HCl sample 3. Dilutions are again prepared by mixing the stock solution with water in different ratios based on volume, producing samples with 2× (1:1 stock and water), 4×, 8×, 16× and 32× dilutions. The diluted samples are kept at 37° C., and the rates at which flocculation/precipitation occurred are monitored. Twenty-four hours from mixing, visible precipitations are observed in systems with 2×, 4× and 8× dilutions. The pH values of the diluted systems are measured at the end of the 24 hour treatment period, and they are 5.57, 5.69, 5.89, 6.06, 6.28 for systems with 2×, 4×, 8×, 16× and 32× dilutions, respectively. These pH values are well within the 5.5 to 10 range suitable for oral care applications.

A third dilution experiment is carried out using ZnO-TMG sample 1. Dilutions are again prepared by mixing the stock solution with water in different ratios based on volume, producing samples with 2× (1:1 stock and water), 4×, 8×, 16× and 32× dilutions. The diluted samples are kept at 37° C., and the rates at which flocculation/precipitation occurred are monitored. One hour from mixing, no visible precipitations can be observed in any samples.

Preparations that generate flocculation/precipitation can be utilized to deposit active agents onto oral surfaces, including dental and mucosal surfaces. In this regard, dilutions from 2× through 8× can be utilized. In the event that the stock solution is prepared at a different concentration, the dilutions that produce the same effective zinc loadings can be used. In an actual formulation, of course, the concentration of zinc in the formulation would be lower than the dilution concentration relative to water, because the total formulation would comprise components in addition to water. Preparations at the low and high ends of the concentration spectrum tend to require longer hours of treatment and are not among the most reliable in producing precipitation/flocculation.

Preparations that do not generate flocculation/precipitation discernible to the naked eyes may also be used for depositing active agents onto oral surfaces. The failure to generate noticeable flocculation/precipitation may be due to unfavorable dilution ratio or inadequate treatment duration. However, the preparations may still be able to generate particles, such as colloidal particles. While these particles do not form precipitates within the treatment duration, they may form surface deposits onto oral surfaces. In this regard, the operable ranges of dilution ratios and/or treatment durations are wider than what can be directly inferred from the above-mentioned dilution experiments.

In some embodiments, the precipitates or particles formed upon dilution comprise one or more types of zinc salts, as well as TMG. In some embodiments, the zinc salts are primarily free from zinc oxide, and are in a form that can be at least partially solubilized in the oral cavity. In some embodiments, one type of the zinc salts is zinc hydroxide. In some embodiments, TMG is also present in the precipitates or particles, either as an integral component thereof, or as an impurity.

ZnO-TMG-HCl provides relatively high levels of solubilized zinc compared what can be delivered from ZnO alone, and moreover provides localized and enriched delivery to dental surfaces (such as dentine and enamel surfaces) upon dilution. The delivered material exists in a form of a solid coating. The coating improves the whiteness of the dental surface. The coating can block dentine tubules providing relief from sensitivity. The coating can neutralize acids providing anti-erosion benefits. The coating can disintegrate in saliva and/or upon acid challenge, and release zinc ions and TMG over an extended period of time, providing all benefits associated with zinc and TMG.

Example 2

Test dentifrice comprising ZnO-TMG HCl, 1450 ppm fluoride, and phosphates is prepared as follows:

TABLE 4

| Ingredient | Wt % |
|---|---|
| PEG600 | 3 |
| CMC-7 | 0.65 |
| Xanthan | 0.2 |
| Sorbitol | 27 |
| Glycerin | 20 |
| Saccharin | 0.3 |
| Tetrasodium pyrophosphate | 0.5 |
| Calcium pyrophosphate | 0.25 |
| Sodium phosphate dibasic | 3.5 |
| Sodium fluoride | 0.32 |
| Titanium dioxide | 0.5 |
| Abrasive silica | 8 |
| Thickener silica | 8 |
| TMG-HCl | 5 |
| Sodium lauryl sulfate | 1.5 |
| Flavoring | 1.2 |
| ZnO | 2 |
| Water | QS |

Example 3

A stable mouthwash formulation is provided as follows:

TABLE 5

| Ingredient | Wt % |
|---|---|
| Sorbitol | 7.5 |
| Glycerin | 7.5 |
| Propylene glycol | 7 |
| Sodium saccharin | 0.02 |
| Citric acid (anhydrous) | 0.05 |
| ZnO | 2 |
| TMG HCl | 5 |
| Flavor/dye | 0.12 |
| Potassium sorbate | 0.05 |
| Cocamidopropyl betaine | 1 |
| Water | QS |

Example 4

Sample 4, ZnO-TMG-HCl, is prepared as follows. 15.3604 g (0.1000 mole) of TMG-HCl (CAS#590-46-5) is dissolved in 100 mL deionized water under stirring. At room temperature, 8.1370 g (0.09999 mole) of zinc oxide powder is slowly added to the TMG-HCl solution. The mixture is stirred overnight for about 16 hours. Unreacted zinc oxide is removed by centrifuging followed by filtering through a 0.45 micron membrane. The final product is a transparent solution.

TABLE 6

| SAMPLE 4 | ZnO | TMG-HCl |
|---|---|---|
| Amount added | 8.1370 g, 0.09999 mol | 15.3604 g, 0.1000 mole |
| pH of final solution | | 6.02 |

A dilution experiment with Sample 4 is carried out to evaluate its ability to form precipitation and/or flocculation upon dilution within a short period of time.

Prior to dilution, the stock solution of Sample 4 and deionized water are preheated to 37° C. Dilutions are prepared by mixing the stock solution with water in different ratios based on volume, producing samples with 1.5× (1 mL of stock and 0.5 mL of water), 2× (1 mL of stock and 1 mL of water), 4× (1 mL of stock and 3 mL of water), 8× (1 mL of stock and 7 mL of water), 16× (0.5 mL of stock and 7.5 mL of water) and 32× (0.5 mL of stock and 15.5 mL of water) dilutions. Upon initial mixing, the samples are manually shaken to maintain effective mixing under ambient conditions (air temperature at about 24° C.). The rates at which flocculation/precipitation occurred are monitored.

It is discovered that the dilutions produce precipitation and/flocculation at different rates. The dilution at 1.5× produced flocculation discernible by the naked eyes within about 20 seconds from initial mixing. The dilution at 2× produced flocculation within about 5 seconds. The dilutions at 4× and 8× require about 10 seconds before flocculation are discernible by naked eyes. The dilution at 16× requires about 1 minute. The dilution at 32× does not produce discernible flocculation by the naked eyes up to 2 minutes from initial mixing.

It is also discovered that similar rates can be acquired at temperatures lower than 37° C., which is the case in the initial stage of use by a typical user. For this, dilutions at 1.5× and 2× are prepared by mixing the Sample 4 stock solution (preheated to 37° C.) and water (at ambient temperature, about 24° C.) in the volumes as recited above. The temperatures of the dilutions are lower than 37° C. The dilutions produced flocculations within the same 20 seconds and 5 seconds time frame, respectively.

The flocculation generated from these short treatments can also attach to dental and mucosal surfaces, delivering zinc-containing compounds and TMG to the target surface. All the benefits discussed with reference to the above-mentioned ZnO-TMG-HCl samples (Samples 2 and 3) apply.

The short duration treatments are uniquely suitable for oral care applications, particularly when delivery is made through toothpaste and mouthrinse. A typical user will brush or rinse for less than 2 minutes. The user's compliance with the regimen will be greatly improved, compared to the situations when lengthy treatment periods are required.

The efficacy with short treatment durations is also expected with the other ZnO-TMG-HCl samples, i.e., Samples 2 and 3.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the scope of the invention should be construed broadly as set forth in the appended claims.

The invention claimed is:

1. An oral care composition comprising an effective amount of an ionic complex of zinc oxide and trimethylglycine (TMG), in free or orally acceptable salt form; wherein the zinc oxide is solubilized in the formulation, but forms a zinc precipitate upon dilution with saliva and/or rinsing.

2. The composition of claim 1 wherein the TMG is in an orally acceptable acid addition salt form.

3. The composition of claim 1 wherein the TMG is in the form of the hydrochloride salt.

4. The composition of claim 3, wherein the zinc oxide and TMG form soluble complexes selected from zinc-TMG-chloride complexes, zinc-chloride complexes, and mixtures thereof.

5. The composition of claim 3, wherein the composition forms a zinc oxide-TMG-HCl complex.

6. The composition of claim 3, wherein the composition comprises a zinc-TMG-HCl complex.

7. The composition of claim 3, wherein the zinc oxide and TMG form two soluble complexes, one having the chemical composition $Zn_2O_8H_6Cl_2$, and the other having the chemical composition $Zn_2O_8H_5Cl_2$-TMG.

8. The composition of claim 1 wherein the amount of zinc is 0.05-4% by weight.

9. The composition of claim 1 wherein the TMG is in the form of a hydrohalide salt, and wherein the molar ratio of zinc oxide to TMG is from 1:1 to 1:10.

10. The composition of claim 1 wherein the complex of the zinc oxide and TMG is prepared prior to incorporation in the oral care composition.

11. The composition of claim 1 in the form of a toothpaste, gel, mouthwash, powder, cream, strip, or gum.

12. The composition of claim 1 further comprising an effective amount of a fluoride ion source.

13. The composition of claim 1 further comprising an orally acceptable base comprising ingredients selected from an abrasive, a buffering agent, a humectant, a surfactant, a thickener, a gum strip or fragment, a breath freshener, a flavor, a fragrance, a colorant, an antibacterial agent, a whitening agent, an agent that interferes with or prevents bacterial attachment, a calcium source, a phosphate source, an orally acceptable potassium salt, an anionic polymer, and combinations of two or more thereof.

14. The composition of claim 1 wherein the pH of the complex is from pH 5 to pH 8.

15. The composition of claim 1 for use to reduce and inhibit acid erosion of the enamel, clean the teeth, whiten teeth, reduce bacterially-generated biofilm and plaque, reduce gingivitis, inhibit tooth decay and formation of cavities, and/or reduce dentinal hypersensitivity.

16. The composition of claim 1, wherein the TMG is in the form of a hydrohalide salt, and the zinc oxide and TMG form soluble complexes selected from zinc-TMG-halide complexes, zinc-halide complexes, and mixtures thereof.

\* \* \* \* \*